United States Patent [19]

Newman

[11] Patent Number: 5,296,480
[45] Date of Patent: Mar. 22, 1994

[54] ANGIOTENSIN II RECEPTOR BLOCKING 2,3,6-SUBSTITUTED 5,6,7,8-TETRA-HYDRO-PYRIDO[4,3]PYRIMIDIN-4(3H)-ONES

[75] Inventor: Howard Newman, Monsey, N.Y.

[73] Assignee: American Cyanamid Company, Wayne, N.J.

[21] Appl. No.: 52,938

[22] Filed: Apr. 23, 1993

[51] Int. Cl.$^5$ .................. A61K 31/505; C07D 471/04; C07F 7/10
[52] U.S. Cl. ...................... 514/258; 544/229; 544/279; 546/14; 546/242; 548/250; 556/418
[58] Field of Search ................. 544/279, 229; 514/258

[56] References Cited

U.S. PATENT DOCUMENTS 5,202,322 4/1993 Allen .............................. 514/228.2

FOREIGN PATENT DOCUMENTS 407342 1/1991 European Pat. Off. .
411766 2/1991 European Pat. Off. .
445811 9/1991 European Pat. Off. .
481448 4/1992 European Pat. Off. .
512870 11/1992 European Pat. Off. .

Primary Examiner—Emily Bernhardt
Attorney, Agent, or Firm—Thomas S. Szatkowski

[57] ABSTRACT

The invention provides compounds having the formula

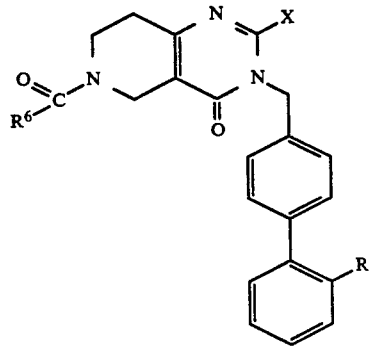

wherein R, X and $R^6$ are defined in the specification which have activity as angiotensin II antagonists.

12 Claims, No Drawings

ANGIOTENSIN II RECEPTOR BLOCKING 2,3,6-SUBSTITUTED 5,6,7,8-TETRA-HYDRO-PYRIDO[4,3]PYRIMIDIN-4(3H)-ONES

BACKGROUND OF THE INVENTION

FIELD OF THE INVENTION

This invention relates to certain novel 2,3,6-substituted 5,6,7,8-tetrahydro-pyrido[4,3-d]pyrimidin-4(3H)-ones which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

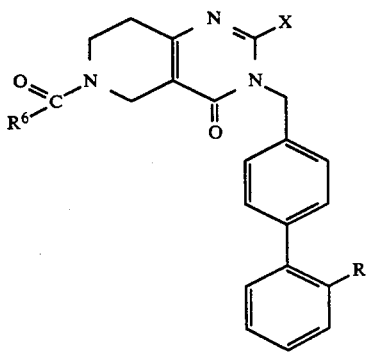

wherein:
R is

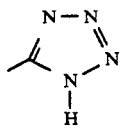

X is straight or branched alkyl of 3 to 5 carbon atoms; $R^6$ is

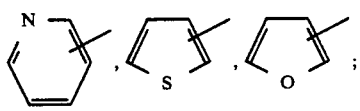

and pharmaceutically acceptable salts of these compounds.

The present invention also provides novel intermediate compounds, methods for making the novel pyrimidin-4(3H)-one angiotensin II antagonizing compounds, methods of using the novel pyrimidin-4(3H)-one angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

As illustrated in Scheme I, to prepare compounds for which $R^6$ is hereinbefore defined, 3-carbethoxy-4-piperidone hydrochloride 1, is reacted with 2-trimethylsilylethyl 4-nitrophenyl carbonate 2 in the presence of aqueous sodium carbonate to give the 2-(trimethylsilyl)ethyl ester 3 after further reaction with sodium dithionite. Reaction of the 2-(trimethylsilyl)ethyl ester 3 with amidine 4 where X is hereinbefore defined, in the presence of alkoxide yields the appropriate 2-substituted-3,5,7,8-tetrahydro-4-oxo-pyrido[4,3-d]pyrimidine-6(4H)-carboxylate 5. The coupling of 5 with biphenyl tritylprotected tetrazole 6 is accomplished by dissolving the reactants in a suitable solvent such as N,N-dimethylformamide, N,N-dimethylacetamide, N-methylpyrrolidinone, methanol, ethanol, t-butanol, tetrahydrofuran, dioxane, acetone or dimethylsulfoxide in the presence of potassium carbonate or other suitable base such as sodium carbonate, cesium carbonate, sodium hydride, potassium hydride, sodium methoxide, sodium ethoxide, sodium t-butoxide, potassium t-butoxide or lithium methoxide for 2-24 hours, at 20°-80° C. to afford the alkylated pyrido[4,3-d]pyrimidin-4(3H)-one 7 as well as the O-alkylated product 8 which are separated by chromatography. The trimethylsilyl ester is removed by reaction of 7 with tri-n-butylammonium fluoride in tetrahydrofuran to give the amine 9. Reaction of azide 10 where $R^6$ is hereinbefore defined with amine 9 in ethyl acetate at room temperature gives acylated product 11. Deprotection of the trityl group on 11 is accomplished by treatment with a catalytic amount of hydrochloric acid in acetone or other suitable acid such as sulfuric, trifluoroacetic or hydrogen chloride for 1-24 hours or by heating in tetrahydrofuran-methanol or methanol to afford the pyrido[4,3-d]pyrimidin-4(3H)-one 12.

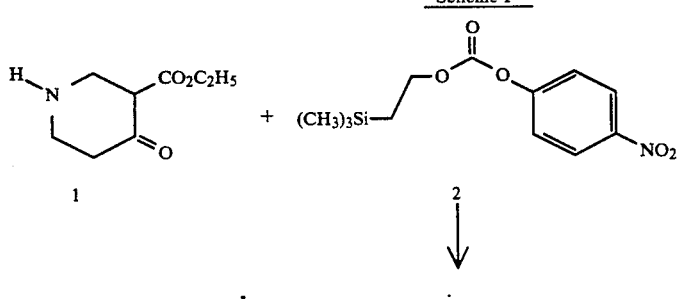

Scheme I

-continued
Scheme I
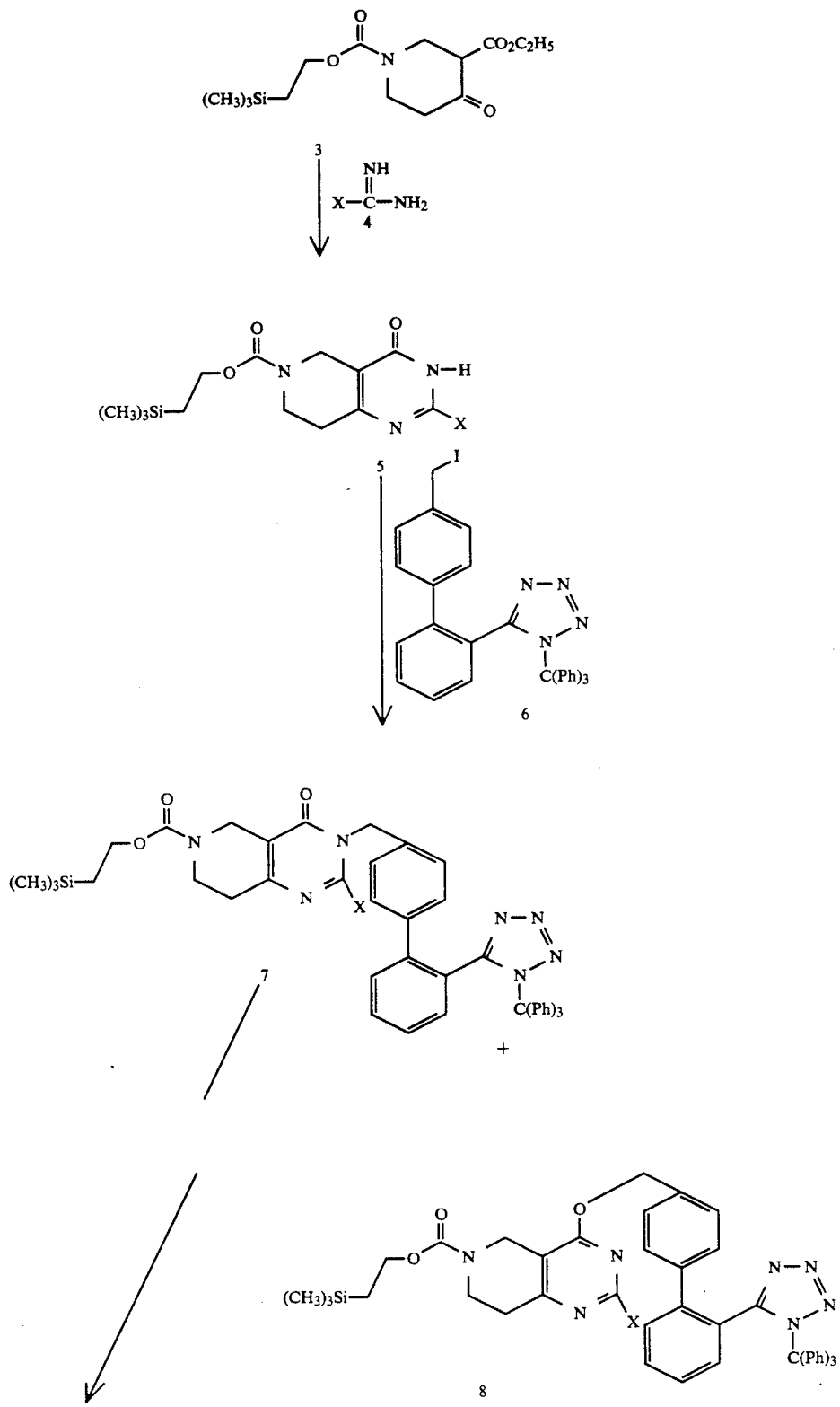

Scheme I -continued

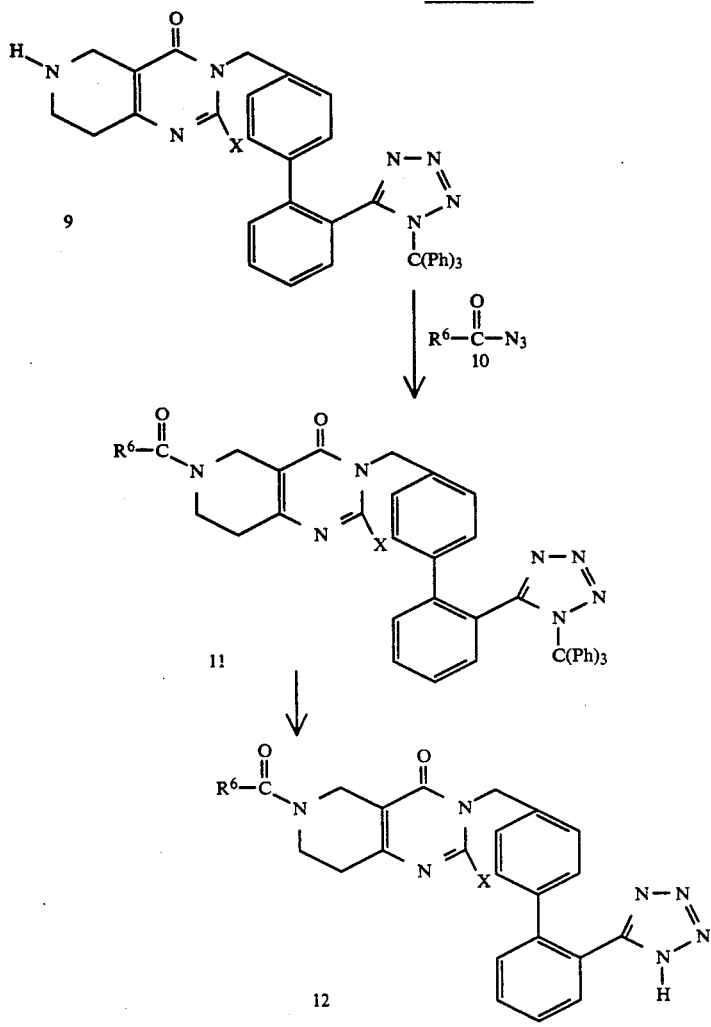

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation can be understood further by the following examples, but should not constitute a limitation thereof.

EXAMPLE 1

Methyl valerimidate hydrochloride

A solution of 16.5 g of valeronitrile and 9 ml of anhydrous methanol in 75 ml of isopropyl ether is cooled in ice and 8.02 g of gaseous HCl bubbled into the reaction mixture. The reaction mixture is refrigerated for 70 hours. A crystalline solid forms and is filtered, washed with isopropyl ether and dried under vacuum for 2 hours to afford 15.7 g of the desired product as a white crystalline solid, m.p. 81°-84° C.

EXAMPLE 2

Valeramidine hydrochloride

To 40 ml of anhydrous methyl alcohol is added 11.7 g of methyl valerimidate hydrochloride and the reaction mixture is cooled in ice while excess gaseous ammonia is added over 5 minutes. A colorless precipitate forms and is rapidly dissolved. The cooling bath is removed and the colorless solution kept at room temperature for 22 hours then evaporated. The concentrate is evaporated under high vacuum for 5 hours to afford 10.3 g of the desired product as a colorless oily solid.

EXAMPLE 3

4-Oxo-1,3-piperidinedicarboxylic acid 3-ethyl-1-[2-(trimethylsilyl)ethyl]ester To a stirred suspension of 2.0 g of 3-carbethoxy-4-piperidone hydrochloride in 20 ml of 1N sodium carbonate at room temperature is added 2.8 g of 2-trimethylsilylethyl 4-nitrophenyl carbonate. The reaction mixture is stirred at room temperature for 3 days and 7.3 g of sodium dithionite added followed by the addition of crushed ice. The reaction mixture is acidified with 3N HCl and extracted with methylene chloride. The organic layer is separated and dried with $Na_2SO_4$ and concentrated in vacuo to give 2.7 g of the desired product as a yellow oil.

EXAMPLE 4

2-Butyl-3,5,7,8-tetrahydro-4-oxo-pyrido[4,3-d]pyrimidine-6(4H)-carboxylic acid 2-(trimethylsilyl)ethyl ester To a mixture of 2.2 g of 4-oxo-1,3-piperidinedicarboxylic acid 3-ethyl 1-[2-(trimethylsilyl)ethyl]ester and 1.2 g of valeramidine hydrochloride in 15 ml of dry ethyl alcohol is added 7 ml of 1M sodium methoxide in methanol. The resulting mixture is stirred and heated under reflux for 25 minutes. The reaction mixture is allowed to cool, filtered and the solid washed with ethyl alcohol. The combined filtrates are evaporated in vacuo without heat to give an oily solid. Ether and water are added to the residue followed by refrigeration. The resulting crystalline solid is collected, washed with ether and air dried to give 0.8 g of the desired product as a crystalline solid, m.p. 152°-155° C.

EXAMPLE 5

5-[4'-(iodomethyl)[1,1'-biphenyl]-2-yl]-1-(triphenylmethyl)-1H-tetrazole

A mixture of 4.0 g of 5-[4'-(bromomethyl)[1,1'-biphenyl]-2-yl]-1-(triphenylmethyl)-1H-tetrazole and 2.2 g of potassium iodide in 50 ml of acetone is heated at reflux for 50 minutes. The reaction mixture is filtered and the filtrate evaporated in vacuo to a residue which is stirred with cold water and the resulting solid collected by filtration, washed with water and air dried to give 4.1 g of the desired product as a solid.

EXAMPLE 6

2-Butyl-3.5,7.8-tetrahydro-4-oxo-3-[[2'-[1-(triphenylmethyl)-1H-tetrazol-5-yl][1,1'-biphenyl]-4-yl]methyl]-pyrido[4,3-d]pyrimidine-6(4H)-carboxylic acid 2-trimethylsilyl)ethyl ester To a stirred solution of 351 mg of 2-butyl-3,5,7,8-tetrahydro-4-oxo-pyrido[4,3-d]-pyrimidine-6(4H)-carboxylic acid 2-(trimethylsilyl)ethyl ester in 2 ml of dry methanol at room temperature is added 1 ml of 1M lithium methoxide in methanol. After stirring at room temperature for 1.5 hours the reaction mixture is evaporated to a residue. The residue is dissolved in 4 ml of dry N,N-dimethylformamide and 605 mg of 5-[4'-(iodomethyl)[1,1'-biphenyl]-2-yl]-1-(triphenylmethyl)-1H-tetrazole added. The reaction mixture is stirred at room temperature for 1 hour, poured into water and the resulting solid collected and dried to give 727 mg of colorless solid. The solid is dissolved in tetrahydrofuran and applied to silica gel thick layer chromatography plates. The plates are eluted with 1:4 ethyl acetate-hexanes to give 132 mg of colorless foam as the O-alkylated product 850(FABMS)(M+Na) and 299 mg of the desired product as a colorless foam 850(FABMS)(M-+Na).

EXAMPLE 7

2-Butyl-5,6,7,8-tetrahydro-3-[[2'-[1-(triphenylmethyl)-1H-tetrazol-5-yl[1,1'-biphenyl]-4-yl]methyl]pyrido4,3-d]pyrimidin-4(3H)-one To a solution of 279 mg of 2-butyl-3,5,7,8-tetrahydro-4-oxo-3-[[2'-[1-(triphenylmethyl)-1H-tetrazol-5-yl][1,1'-biphenyl]-4-yl]methyl]pyrido[4,3-d]pyrimidine-6(4H)-carboxylic acid 2-trimethylsilyl ethyl ester in 5 ml of dry tetrahydrofuran is added 0.5 ml of 1M tri-n-butylammonium fluoride in tetrahydrofuran. The reaction mixture is heated at reflux for 15 minutes then evaporated in vacuo to a residue. The residue is diluted with water, stirred for 15 minutes, the solid collected, washed with water and dried to give 238 mg of the desired product as a colorless amorphous solid.

EXAMPLE 8

Nicotinyl Azide

A mixture of 1.8 ml of HCl and 1.5 g of nicotinyl hydrazide is cooled in ice-water and pieces of ice added to keep the temperature below 10° C. A solution of 1.5 g of sodium nitrite in 2.5 ml of water is added dropwise over 5-10 minutes. The reaction mixture is extracted with ether and the organic layer washed with aqueous sodium bicarbonate, dried and evaporated to a residue which is dissolved in 2-3 ml of water and the pH adjusted to weakly basic with aqueous sodium bicarbonate. The resulting solid is collected and dried to give 36 mg of the desired product as a colorless solid, m.p. 40°-43° C.

EXAMPLE 9

2-Butyl-5,6,7,8-tetrahydro-6-(3-pyridinylcarbonyl)3-[2'-[1-(triphenylmethyl)-1H-tetrazol-5-yl][1,1'-biphenyl]-4-yl]methyl]pyrido[4,3-d]pyrimidin-4(3H)-one To a stirred solution of 100 mg of 2-butyl-5,6,7,8-tetrahydro-3-[[2'-[1-(triphenylmethyl)-1H-tetrazol-5-yl][1,1'-biphenyl]-4-yl]methyl]pyrido[4,3-d]pyrimidin-4(3H)-one in 2 ml of ethyl acetate is added 22 mg of nicotinyl azide. The reaction mixture is stirred at room temperature for 16 hours and the volatiles evaporated in vacuo to give the desired product as a yellow-orange foam.

EXAMPLE 10

2-Butyl-5,6,7,8-tetrahydro-6-(3-pyridinylcarbonyl)-3-[2'-(1H-tetrazol-5-yl)[1,1'-biphenyl]-4-yl]methyl]-pyrido[4,3-d]pyrimidin-4(3H)-one The entire sample of Example 9 is dissolved in 5 ml of absolute methyl alcohol and heated at reflux for 3 hours. The volatiles are evaporated to a residue which is stirred with ether and decanted two times. The residue is dried under high vacuum to give 86 mg of the desired product as a light yellow foam.

Utility

The performance of the novel compounds of the present invention are shown in the following In Vitro test. The results of this test for representative compounds of the present invention are shown in Table I.

Angiotensin II Antagonists In Vitro Tests

Receptor Binding Assay

Binding of [$^{125}$I](Sar$^1$, Ile$^8$)AngII

The binding of [$^{125}$I](Sar$^1$,Ile$^8$)AngII to microsomal membranes is initiated by the addition of reconstituted membranes (1:10 vols.) in freshly made 50.0 mMTris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AngII (Specific Activity, 2200 Ci/mmole). Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethylenemine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their IC$_{50}$ values. The results are shown in Table I.

TABLE I

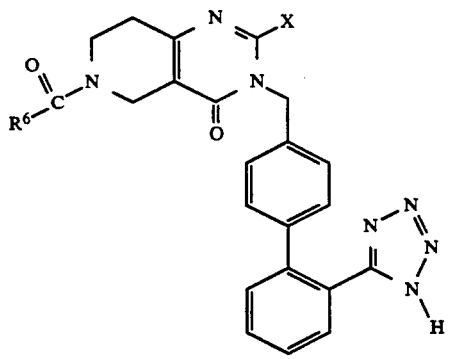

| Ex. No. | R$_6$ | X | Angiotensin II Receptor Binding IC$_{50}$ (M) |
|---|---|---|---|
| 10 | ![pyridyl] | —(CH$_2$)$_3$CH$_3$ | 5.1 × 10$^{-8}$ |

The enzyme renin acts on a blood plasma globulin, angiotensinogen, to produce angiotensin I, which is then converted by angiotensin concerting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

As can be seen from Table I, the compounds demonstrate excellent Angiotensin II Receptor Binding activity.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint or ease of preparation and administration are solid compositions, particularly tablets and hard filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid Polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol(e.g., glycerol, propylene glycol and liquid polyethylene glycol), suitable mixtures thereof, and vegetable oils.

What is claimed is:

1. A pyrimidinone compound having the formula:

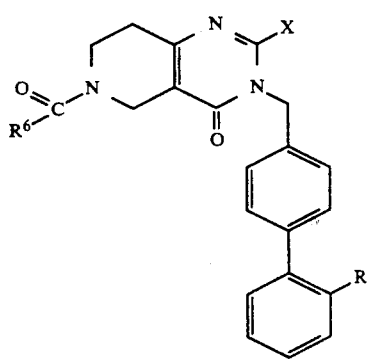

wherein:
R is

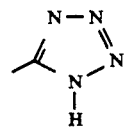

X is a straight or branched alkyl of 3 to 5 carbon atoms;
R⁶ is

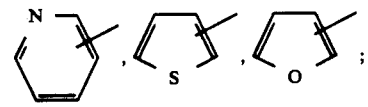

or pharmaceutically acceptable salts of these compounds.

2. The compound according to claim 1 wherein said salts are selected from potassium, sodium, calcium, magnesium or ammonium.

3. The compound according to claim 1 wherein
X is a straight chain alkyl of 3 to 4 carbon atoms;
R⁶ is

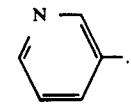

4. A pyrimidinone compound having the formula:

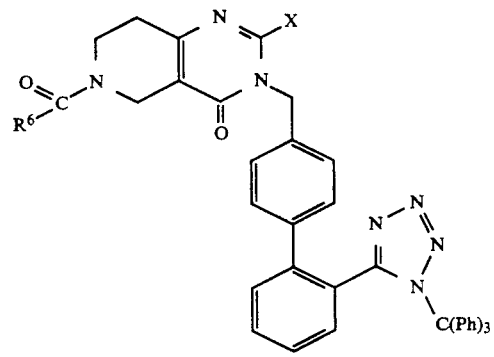

wherein
X is a straight or branched alkyl of 3 to 5 carbon atoms;
R⁶ is

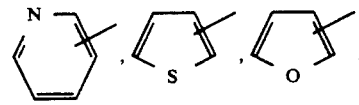

5. The compound according to claim 4 wherein
X is a straight chain alkyl of 3 or 4 carbon atoms;
R⁶ is

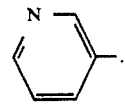

6. A pyrimidinone compound having the formula:

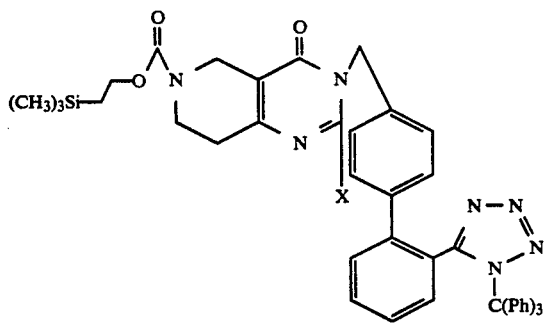

wherein: X is a straight or branched alkyl of 3 to 5 carbon atoms.

7. The compound according to claim 1 2-Butyl-5,6,7,8-tetrahydro-6-(3-pyridinylcarbonyl)-3-[-[2'-(1H-tetrazol-5-yl) [1,1'-biphenyl]-4-yl]methyl]pyrido[4,3-d]pyrimidin-4(3H)-one.

8. The compound according to claim 4 2-Butyl-5,6,7,8-tetrahydro-6-(3-pyridinylcarbonyl)-3-[2'-[1-(triphenylmethyl)-1H-tetrazol-5-yl][1,1'-biphenyl]-4-yl]methyl]pyrido[4,3-d]pyrimidin-4(3H)-one.

9. A pharmaceutical composition useful for treating angiotensin induced hypertension or congestive heart failure in a mammal comprising a suitable pharmaceutical carrier and an effective amount of a compound of claim 1.

10. A method of treating angiotensin induced hypertension in a mammal comprising administering a compound of claim 1 to said mammal an amount effective to lower angiotensin induced hypertension.

11. A method of treating congestive heart failure in a mammal comprising administering a compound of claim 1 to said mammal in an amount effective to treat congestive heart failure.

12. A method of antagonizing the effects of Angiotensin II in a mammal comprising administering a compound of claim 1 to said mammal in an amount effective to treat the effects of Angiotensin II.

* * * * *